United States Patent
Henning et al.

(10) Patent No.: US 9,274,041 B2
(45) Date of Patent: Mar. 1, 2016

(54) PARTICLE COUNTER AND CLASSIFICATION SYSTEM

(71) Applicant: Spectro Scientific, Inc., Chelmsford, MA (US)

(72) Inventors: Patrick F. Henning, Concord, MA (US); Eric J. Olson, Phillipston, MA (US); John Glaberson, Sandy Hook, CT (US); Thomas Barraclough, Maynard, MA (US)

(73) Assignee: Spectro Scientific, Inc., Chelmsford, MA (US)

(*) Notice: Subject to any disclaimer, the term of this patent is extended or adjusted under 35 U.S.C. 154(b) by 0 days.

(21) Appl. No.: 14/253,354

(22) Filed: Apr. 15, 2014

(65) Prior Publication Data

US 2015/0293009 A1    Oct. 15, 2015

(51) Int. Cl.
| | |
|---|---|
| *G01N 27/74* | (2006.01) |
| *G01N 27/72* | (2006.01) |
| *G01R 33/12* | (2006.01) |
| *G01R 33/00* | (2006.01) |
| *G01N 21/00* | (2006.01) |
| *G01N 15/10* | (2006.01) |
| *G01N 15/06* | (2006.01) |

(52) U.S. Cl.
  CPC ............ *G01N 15/10* (2013.01); *G01N 15/0656* (2013.01); *G01N 2015/0693* (2013.01); *G01N 2015/1087* (2013.01)

(58) Field of Classification Search
  CPC .......................... G01N 15/10; G01N 15/0656
  USPC ............ 356/72; 324/204, 249, 228, 251, 252, 324/260
  See application file for complete search history.

(56) References Cited

U.S. PATENT DOCUMENTS

| | | | |
|---|---|---|---|
| 4,657,671 A * | 4/1987 | Botstiber et al. | 210/86 |
| 4,686,469 A * | 8/1987 | Lewis | 324/204 |
| 5,001,424 A | 3/1991 | Kellett et al. | |
| 5,170,056 A | 12/1992 | Berard et al. | |
| 5,315,243 A | 5/1994 | Kempster et al. | |
| 5,404,100 A | 4/1995 | Burnett et al. | |
| 5,444,367 A | 8/1995 | Kempster et al. | |
| 5,572,320 A | 11/1996 | Reintjes et al. | |
| 5,627,905 A | 5/1997 | Sebok et al. | |
| 5,708,198 A * | 1/1998 | Fitch et al. | 73/61.42 |
| 5,811,664 A | 9/1998 | Whittington et al. | |
| 5,959,668 A | 9/1999 | Cryder et al. | |
| 6,049,381 A | 4/2000 | Reintjes et al. | |
| 6,051,970 A | 4/2000 | Hutchings | |
| 6,104,483 A | 8/2000 | Sebok et al. | |

(Continued)

*Primary Examiner* — Kara E Geisel
*Assistant Examiner* — Hina F Ayub
(74) *Attorney, Agent, or Firm* — Iandiorio Teska & Coleman, LLP

(57) ABSTRACT

A particle counter and classification system including an imaging subsystem configured to determine the size and morphology of particles above a predetermined size in a fluid in a sample cell. A first stage magnetometer sensor subsystem is tuned to detect and determine the size of ferrous and/or conducting particles. An optional second stage magnetometer sensor subsystem is tuned to detect the overall ferrous particle content of the fluid. A processor subsystem is configured to calculate and report the number of particles in the fluid in a plurality of size ranges, their morphology, their classification as a particular particle type according to their characteristic morphology, the number of ferrous and/or conducting particles, and the overall ferrous content of the fluid.

25 Claims, 6 Drawing Sheets

(56) References Cited

U.S. PATENT DOCUMENTS

| | | |
|---|---|---|
| 6,501,504 B1 | 12/2002 | Tatko et al. |
| 6,671,548 B1 * | 12/2003 | Mouchawar et al. ........... 607/14 |
| 6,873,411 B2 | 3/2005 | Sebok et al. |
| 7,019,834 B2 | 3/2006 | Sebok et al. |
| 7,184,141 B2 | 2/2007 | Brewer et al. |
| 7,307,717 B2 | 12/2007 | Kolp et al. |
| 7,385,694 B2 | 6/2008 | Kolp et al. |
| 7,921,739 B2 | 4/2011 | Fjerdingstad et al. |
| 8,056,400 B2 | 11/2011 | Reintjes et al. |
| 8,079,250 B2 | 12/2011 | Sebok et al. |
| 2005/0116712 A1 * | 6/2005 | Corver et al. ................. 324/309 |

* cited by examiner

| Particle Size μ (microns) | Overall Number | Shape | Magnetic Particles | Overall Magnetic Content |
|---|---|---|---|---|
| 4 | 7,122 | — | — | 2.0 PPM |
| 5 | 2,116 | — | — | |
| 6 | 324 | — | — | |
| 10 | 20 | — | — | |
| 14 | 10 | — | — | |
| 15 | 7 | — | 2 | |
| 20 | 7 | 3 cutting wear<br>4 sliding wear | 6 | |
| 21 | 5 | 4 cutting wear<br>1 sliding wear | 4 | |
| 25 | 4 | 3 cutting wear<br>1 sliding wear | 4 | |
| 38 | 3 | 3 cutting wear | 3 | |
| 50 | 2 | 2 sliding wear | 2 | |
| 70 | 2 | 1 cutting wear<br>1 sliding wear | 2 | |
| 100 | 1 | 1 cutting wear | 1 | |

*FIG. 3*

PARTICLE COUNTER AND CLASSIFICATION SYSTEM

FIELD OF THE INVENTION

This invention relates to particle counters, magnetometers, and the classification of particulate in a fluid via particle imaging.

BACKGROUND OF THE INVENTION

The number of particles in a fluid sample, their size, and shape (morphology) can be determined by an imaging apparatus as shown, for example, in U.S. Pat. Nos. 5,572,320; 7,385,694; 5,627,905; 5,959,668; 6,049,381; 6,104,483; 6,501,504; 6,873,411; 7,019,834; 7,184,141; 7,307,717; 7,385,694; 7,921,739; 8,056,400 and 8,079,250 all incorporated herein by this reference. There is typically, however, no differentiation made between magnetic and non-magnetic particles. This information is important to maintenance personnel.

Magnetometers can be used to determine the overall percent of ferromagnetic particles in oil, or to provide information regarding the size and magnetic nature (ferromagnetic or non-ferromagnetic) of individual particles greater than a certain minimum size threshold. See, for example, U.S. Pat. Nos. 5,001,424; 5,315,243; 5,444,367; 5,404,100; 5,811,664 and 6,051,970 all incorporated herein by this reference. Such devices, however, do not classify the magnetic particles according to morphology. In addition, such devices typically either supply an overall ferromagnetic percent or information regarding individually observed particulate, but not both.

SUMMARY OF THE INVENTION

A particle counter and classification system with an imaging apparatus and a magnetometer type device enables, for example, the user to determine which particles of a given shape or size is either (1) ferromagnetic, (2) non-ferromagnetic and electrically conducting or (3) non-ferromagnetic and non-conducting.

In one example, a particle counter and classification system provides for the determination of the size and shape of magnetic and conducting particles, quantifies magnetic and conducting particles, and in one example, separately analyzes non-metallic particles.

In one preferred embodiment, a dual-stage magnetometer is positioned behind an analysis cell associated with a particle imaging apparatus. In this way, particles from the same fluid can be imaged and counted. These same particles can then be characterized for their individual magnetic and conducting content using the dual-stage magnetometer. Finally, the dual-stage magnetometer can report the overall magnetic content of the fluid, which allows for particles which are too small to be imaged or characterized individually to be accounted for.

Featured is a particle counter and classification system comprising an imaging subsystem configured to determine the size and morphology of particles above a predetermined size in a fluid in a sample cell. A first stage magnetometer sensor subsystem for the fluid is tuned to detect and determine the size of ferrous and/or conducting particles in the fluid above the predetermined size. A second stage magnetometer sensor subsystem for the fluid is tuned to detect the overall ferrous particle content of the fluid. A processor subsystem is responsive to the imaging subsystem, the first stage magnetometer sensor subsystem, and the second stage magnetometer sensor subsystem. The processor subsystem is configured to calculate and report the number of particles in the fluid in a plurality of size ranges, their morphology, their classification as a particular particle type according to their characteristic morphology, the number of ferrous and/or conducting particles in said size ranges, and the overall ferrous content of the fluid.

The imaging subsystem may include a light source directing electromagnetic radiation into the sample cell and a detector responsive to electromagnetic radiation emitted from the sample cell. The first stage magnetometer sensor subsystem may include a small diameter fluid conduit upstream or downstream of the sample cell with a small diameter sense coil thereabout and the second stage magnetometer sensor subsystem may include a larger diameter fluid conduit downstream of the sample cell with a larger diameter sense coil thereabout. The larger diameter fluid conduit may be downstream of a small diameter fluid conduit. The filling factor of the small diameter sense coil is preferably optimized for ferrous and/or conducting particles imageable by the imaging subsystem. The filling factor of the large diameter sense coil is preferably optimized for ferrous particle sizes below and above said predetermined size. The first stage magnetometer sensor subsystem may further include an impedance monitor configured to detect the amplitude and phase of the voltage of the small diameter sense coil. The second stage magnetometer sensor subsystem may further include an impedance monitor configured to detect the amplitude and phase of the voltage of the larger diameter sense coil. In one design, the small diameter conduit is between 250 and 750 microns in diameter and the larger diameter conduit is between 1,500 and 15,000 microns in diameter.

Also featured is a particle counting and classification method. Particles in a fluid are imaged to determine their size and, for particles above a predetermined size, to determine their morphology. Ferrous and/or conducting particles above the predetermined size are detected and, for the ferrous and/or conducting particles above the predetermined size, the number of the ferrous and/or conducting particles in a plurality of size ranges is counted. The method further includes detecting ferrous particles above and below a predetermined size and calculating the overall ferrous particle content of said fluid. Detecting ferrous and/or conducting particles above said predetermined size may include passing the fluid through a first stage magnetometer sensor subsystem with a small diameter fluid conduit having a small diameter sense coil thereabout and detecting ferrous and/or conducting particles above and below the predetermined size includes passing the fluid through a second stage magnetometer sensor subsystem with a larger diameter fluid conduit having a larger diameter sense coil thereabout. Detecting ferrous and/or conducting particles above said predetermined size may include detecting the amplitude and phase of the voltage of the small diameter sense coil. Detecting ferrous particles above and below the predetermined size may include detecting the amplitude and phase of the voltage of the larger diameter sense coil.

Also featured is a particle counter and classification system comprising an imaging subsystem configured to determine the size and morphology of particles above a predetermined size in a fluid in a sample cell, a first stage magnetometer sensor subsystem for the fluid tuned to detect and determine the size of ferrous and/or conducting particles in said fluid above said predetermined size, and a processor subsystem, responsive to the imaging subsystem and the first stage magnetometer sensor subsystem, configured to calculate and report the number of particles in the fluid in a plurality of size ranges, their morphology, their classification as a particular particle type according to their characteristic morphology and the number of ferrous and/or conducting particles in said size ranges.

The system may further include a second stage magnetometer sensor subsystem for said fluid tuned to detect the overall ferrous particle content of the fluid. The processor subsystem is configured to initially classify said particles in different size ranges based on the output of said imaging subsystem and to adjust said initial classification based on the output of said first stage magnetometer sensor subsystem.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features, and advantages will occur to those skilled in the art from the following description of a preferred embodiment and the accompanying drawings, in which:

FIG. 3 is a schematic view showing a report displayed on the display shown in FIG. 1 generated by the processor subsystem of FIG. 1;

DETAILED DESCRIPTION OF THE INVENTION

Figure 1:
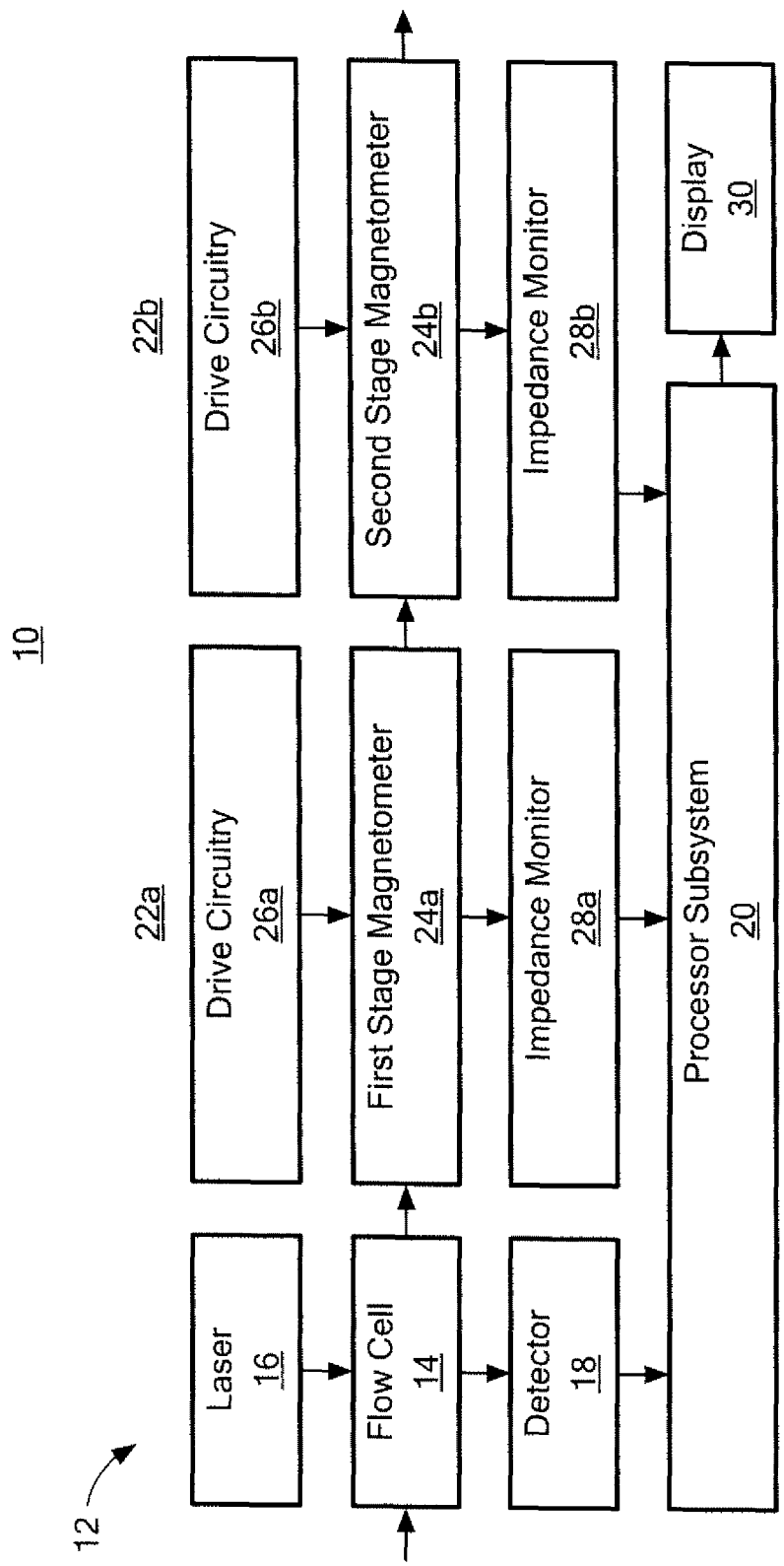
FIG. 1 is a block diagram showing the primary components associated with an example of a particle counter and classification system in accordance with the invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 depicts an example of a particle counter and classification system 10 including imaging subsystem 12 with flow cell 14 through which a fluid (e.g., oil) sample passes. The sample may be fluid diverted via a bypass conduit in a machine (e.g., engine or motor) or may be a sample obtained from a machine and delivered to an analyzer. Laser 16 directs electromagnetic radiation into sample cell 14 and detector 18 (including, for example, a CCD) images the contents of the cell as is known in the art.

Electronic signals output by detector 18 concerning the number, size, and shape of particles in the fluid is processed by processor subsystem 20 responsive to detector 18. Processor subsystem 20 may be a computer, a microprocessor based electronic subsystem, a field programmable gate array appropriately programmed, an application specific integrated circuit or the like. The processor subsystem may be distributed amongst various devices and/or circuitry in some examples.

Imaging subsystem 12 is configured (using optical devices if necessary) to focus appropriately on certain size particles of interest, typically between 20 and 100 microns. Imaging subsystem 12, for certain particle size ranges, can detect the particles, determine their size, determine their morphology (shape) and processor subsystem 20 can include algorithms to categorize the particles (for example, particles generated by cutting wear, particles generated by sliding wear, and the like). The depth of field necessary to sharply image particles of interest can be configured and/or adjusted as necessary. The imaging subsystem, however, can also detect and determine the size of smaller particles such as particles between 4 microns and 20 microns. For those particles, however, the imaging subsystem cannot typically determine their shape nor can they be categorized.

Figure 2:
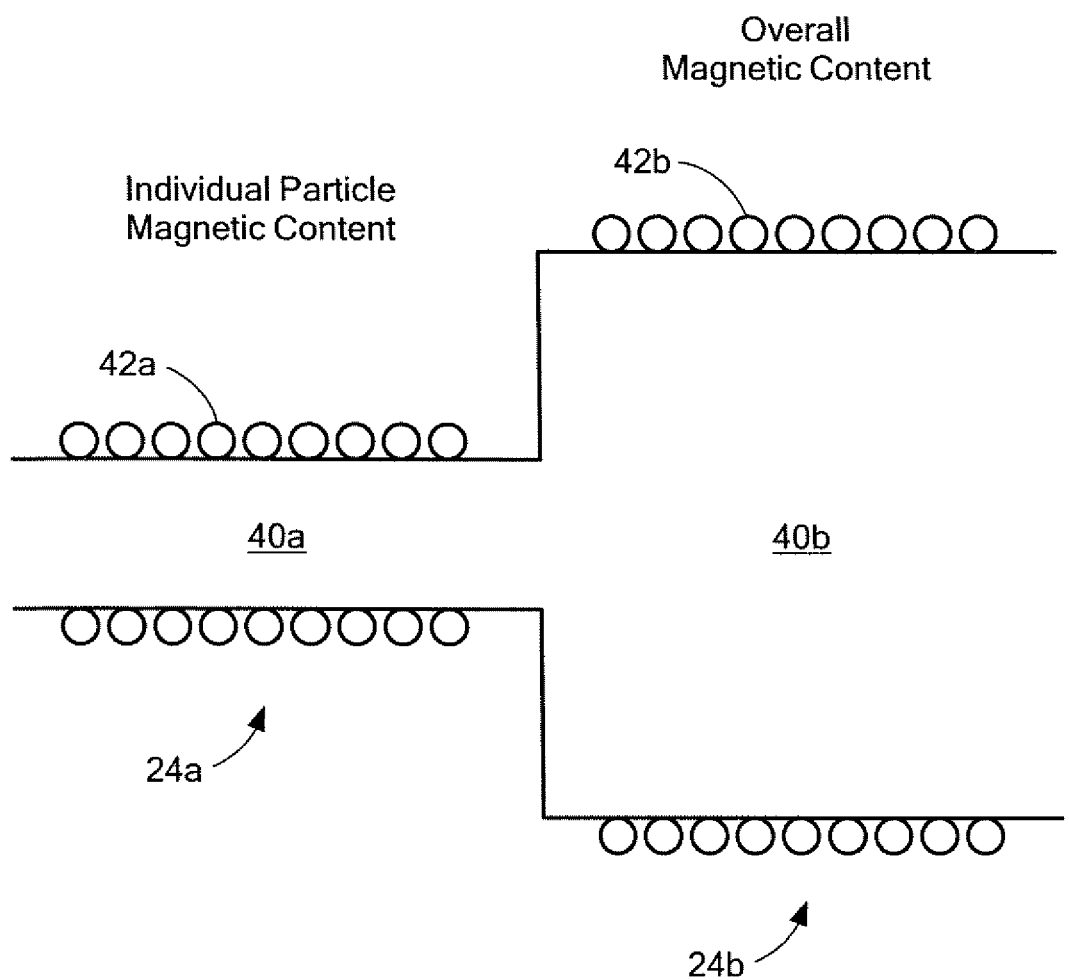
FIG. 2 is a schematic cross sectional view showing portions of the first and second stage magnetometer sensor subsystems associated with the system shown in FIG. 1.

After passing through cell 14 the fluid proceeds or is delivered to first stage magnetometer sensor subsystem 22a tuned to detect and determine the size of ferrous and/or conducting particles in the fluid imaged by the imaging subsystem 12. Note that the fluid may also be delivered first to magnetic sensor subsystem 22a and then to cell 14. In this particular example, first stage magnetometer sensor subsystem 22a includes first stage magnetometer head 24a, FIG. 2 typically a plastic fluid conduit with driving and sensing coils thereabout. FIG. 2 depicts only one sense coil 42a for clarity. Drive circuitry 26a, FIG. 1 energizes the drive coil(s) and impedance monitor 28a reports the amplitude and phase change of the voltage sense coil(s) representing the presence of ferrous and/or conducting particles passing through the small diameter (e.g., 500 micron) conduit 40a. This first stage magnetometer sensor subsystem 22a, FIG. 1 may include copper drive windings over copper sense windings. A dummy coil arrangement may be included about a conduit with no fluid flowing through it also having an output directed to processor subsystem 20.

Impedance monitor 28a provides an output signal to processor subsystem 20 configured or programmed to report via display 30 the number of ferrous particles in various size ranges optionally using data obtained from imaging subsystem 12 typically upstream of first stage magnetometer sensor subsystem 24a. The result is a report including the number of particles in each size range (and optionally their shape or other morphology information) and how many of those particles in that size range are ferrous or conducting as shown in FIG. 3.

The second stage magnetometer sensor subsystem 22b, FIG. 1 is preferably located downstream of first stage magnetometer sensor subsystem 22a and includes, as shown in FIG. 2, a much larger (e.g., 15,000 micron) size fluid plastic conduit 40b with driven and sensing coils thereabout such as sense coil 42b. The drive coil(s) are energized by drive circuitry 26b, FIG. 1 and impedance monitor 28b reports the amplitude and phase change of the voltage sense coil(s) to processor subsystem 20. Again, a dummy coil arrangement may be used for second stage magnetometer sensor subsystem 24b. Second stage magnetometer sensor subsystem 22b is tuned to detect the overall ferrous particle content of the fluid and processor subsystem 20 reports this data to display 30 as shown in FIG. 3.

The first stage 22a is specifically designed to be sensitive to particulate for which morphology information can be obtained by the imaging subsystem. The miniature bore magnetometer head is designed so that the filling factor of the sense coil is optimized for particles in a particular equivalent circular diameter range. In one embodiment, this apparatus would be sensitive to particles with equivalent circular diameter of 20 microns and greater. The magnetometer electronics are designed to report the amplitude and phase of the voltage of the sense coil associated with each particle.

The second stage of the magnetometer, in contrast, is designed such that a separate and distinct set of coils, typically with much larger radius, provide an optimal reading of the overall magnetic content of a fluid. Assuming the distribution of particulate of all sizes within the fluid is homogeneous, the overall magnetic content of the fluid increases in a power-law fashion as the radius of the sense coil and fluid flowing through the coil increases. At the same time, the field strength per unit volume of a solenoid need not decrease in such a cubic fashion as the radius of the sense coil increases. Thus, there are many optimal sensitivity designs which include larger radii sense coils which may be chosen to report the overall magnetic content of the fluid. Note that, in general, such coils will not be appropriate for individual particulate since their fill factor for individual particulate will in general be much less. Such a magnetometer can operate separately from the imaging subsystem as well, in cases where no imaging apparatus is required.

In one embodiment, the dual-stage magnetometer includes, for Stage 1, a 2-layer excite/sense solenoid design connected in a bridge arrangement with an identical excite/sense solenoid. Such a 4-coil system is then excited with a drive voltage which is fed into a synchronous demodulation circuit. Once zeroed, such a circuit produces the amplitude and phase of the signal due to individual particles passing through the active solenoid. Through filtering the resulting signal through a band pass circuit based on the expected oscillation profile due to individual particulate, a highly sensitive individual particulate monitoring magnetometer stage is realized. For Stage 2, an identical magnetic design using a much larger solenoid radius is chosen. An identical excitation/demodulation circuit is also chosen but in this case, the (unfiltered) dc signal, which provides the amplitude and phase of the overall magnetic content of the fluid, is probed. Stage 1 and Stage 2 are coupled via flow tubing which is appropriately sized for each stage.

In this way, a unique dual-stage magnetometer arrangement is achieved. Such a dual-stage magnetometer can have substantial benefit relative to conventional magnetometers, including but not limited to, the fact that the signals arising from both stages may be compared to each other to provide further validation and robustness to the particle and overall magnetic content algorithms employed by processor subsystem 20 to determine such quantities.

Using statistical techniques, processor subsystem 20, FIG. 1 presented with signals from imaging subsystem 12, first stage magnetometer sensor subsystem 22a, and optionally second stage magnetometer sensor subsystem 22b and is programmed to calculate and report the number of particles in the fluid in a plurality of size ranges, their shape, the number of ferrous particles in those size ranges, and the over all ferrous content of the fluid. Moreover, the calculations of the ferrous content based on data from first stage magnetometer sensor subsystem 22a and/or second stage magnetometer sensor subsystem 22b can depend on or be based on the data from imaging subsystem 12.

For example, the imaging subsystem 12 may provide an initial classification by identifying all wear debris, which can be either conducting (e.g., Copper) type and/or ferromagnetic (e.g., Iron) type. Based on this classification, the first stage magnetometer subsystem 22a, may then provide a positive identification as to the type of the identified wear debris. The wear debris count and size statistics may then be updated. If as a result of imaging subsystem 12 there were 62 identified wear particles in the 25 micron size bin, and the first stage magnetometer subsystem identifies 55 ferromagnetic particles in the 25 micron size bin, the processor subsystem 20 may report that 88.7% of identified wear debris in the 25 micron size bin was ferrous. Further, if the results show that as a result of subsystem 22a that 128 wear particles are identified as being ferromagnetic, this may indicate that the original wear debris classification of all particulate identified may need to be refined to classify more particles as being wear debris. This may trigger a reclassification of all particulate using modified classification criteria so that the total amount of wear debris in the 25 micron size bin has at least 128 particles. In this way, the first magnetometer subsystem 22a may provide feedback to improve the quality of the classifier operating on imaging subsystem 12. Such calculations concerning the particulate would not be possible without combining the data from subsystems 12 and 22a analyzing the same aliquot of fluid. The processor subsystem 20 may classify individual particulate identified by imaging subsystem 12 as being either cutting, sliding or fatigue wear particles, non-metallic particles, fibers, water droplets, or air bubbles. The processor subsystem 20 may then in turn utilize this information in conjunction with the information provided by the first stage magnetometer subsystem 22a to provide targeted ferrous and conducting particle count information on the specific cutting, sliding, and fatigue wear particles identified using the processor subsystem's analysis of imaging subsystem 12 information. In this example, the processor subsystem 20 may provide magnetic particle count information as a percentage of the total number of cutting, sliding, and fatigue wear particles identified in all size bins (20, 21, 25, 38, 50, 70, 100 microns).

As shown in FIG. 3, the imaging subsystem 12, FIG. 1 is able to detect and count particles between 4 to 100 microns in this example but can only image, size, and classify particles between 20 and 100 microns. For example, in this particular scenario shown, there were five particles 21 microns (or greater) and based on their shape, processing subsystem 20 has classified four of these particles from cutting type wear and one of these particles resulting from sliding type wear as shown in FIG. 3.

First stage magnetometer sensor subsystem 22a, FIG. 1 is tuned to count and size ferrous particles between 20 microns and 100 microns in several size ranges. Note the this information combined with the information provided by the imaging subsystem enables the analyst to readily see that four out of five particles in the size range of 21 microns (or greater) were due to cutting wear and were magnetic. This could indicate to the analyst, for example, that a machine's steel alloy bearings are wearing as opposed to cutting wear shaped particles from an aluminum or other non-ferrous part or subsystem such as an oil pump mostly including non-magnetic components.

Second stage magnetometer sensor subsystem 22b, FIG. 1 is tuned to detect the overall magnetic content and typically provides no size information. Instead, second stage magnetometer sensor subsystem 22b detects particles as small as four microns and as large as 100 microns and, importantly, provides information concerning small size ferrous particles (e.g., 0 to microns) that imaging subsystem 12 and first stage magnetometer sensor subsystem 22a cannot.

Processor subsystem 20 is configured to analyze the signals output by the imaging subsystem 12, first stage magnetometer sensor subsystem 22a, and second stage magnetometer sensor subsystem sensing sensor subsystem 22b as follows.

If a small sized particle (e.g., four microns) is present in a fluid sample, imaging subsystem 12 can detect the particle and determine its size but cannot obtain a sufficient image of the particle in order to determine the shape of such a small particle and/or its category, for example, whether the particle was generated by sliding wear or cutting wear. The output signal of imaging subsystem 12 thus presented to processor subsystem 20 enables processor subsystem 20 to report only the size of this particle and to add it to the count of particles sized four microns (and greater).

First stage magnetometer sensor subsystem 22a typically provides no relevant data concerning such a small sized particle because it is tuned to particles in the size range (e.g., 20 microns to 100 microns) which are fully imageable by the imaging subsystem. Second stage magnetometer sensor subsystem 22b, however, detects this four micron particle if it is a ferrous particle. Knowing the volume of fluid, the processor subsystem 20, responsive to a signal from impedance monitor 28b, adds this particle to the concentration (e.g., parts per million) calculation for ferrous particles in the overall magnetic content report.

When a larger particle (e.g., 25 microns) is present in the fluid sample, imaging subsystem 12 detects this particle and provides a signal regarding its size and shape. Processor subsystem 20 then categorizes this particle based on its shape (e.g., sliding wear, cutting, or the like) and reports the result. Processor subsystem 20 also adds this particle to the count of those size particles in the sample. First stage magnetometer sensor subsystem 22a detects whether this particle is ferrous and/or conducting and if so outputs a signal which enables processor subsystem 20 to size the particle and add it to the count of ferrous and/or conducting particles of that size. If this particle is ferrous, second stage magnetometer sensor subsystem 22b also reports this particle to processor subsystem 20 which adds it to the overall magnetic content parts per million calculations. Thus, for particles greater than 20 microns in size, the output of first stage magnetometer sensor subsystem 22a and second stage magnetometer sensor subsystem 22b provide some redundant information which can either be ignored or used in algorithms to refine the output provided by processor subsystem 20 as it uses the redundant information to make corrections to the final report.

The following chart summarizes the capabilities of each subsystem:

| Size (microns) | Detect | Identify as ferrous | Determine size | Determine shape | Classify |
|---|---|---|---|---|---|
| 4-20 | Imager 2$^{nd}$ stage (if ferrous) | 2$^{nd}$ stage | | | |
| 20-100 | Imager 1$^{st}$ stage (if ferrous) 2$^{nd}$ stage (if ferrous) | 1$^{st}$ stage 2$^{nd}$ stage | Imager 1$^{st}$ stage (if ferrous) | Imager | Imager |

Thus, for particles 20-100 microns in size, the imager combined with the first stage magnetometer sensor subsystem provides key information concerning the same fluid sample. Here, the second stage magnetometer sensor subsystem supplements the first stage for redundancy and robustness.

For particles smaller than 20 microns, e.g., 4-20 microns, the imager detects them and keeps count of particles in various size bins and the second stage magnetometer subsystem enables a more accurate count of the overall magnetic particle concentration in these size ranges where the first stage magnetometer subsystem cannot.

Figure 4:
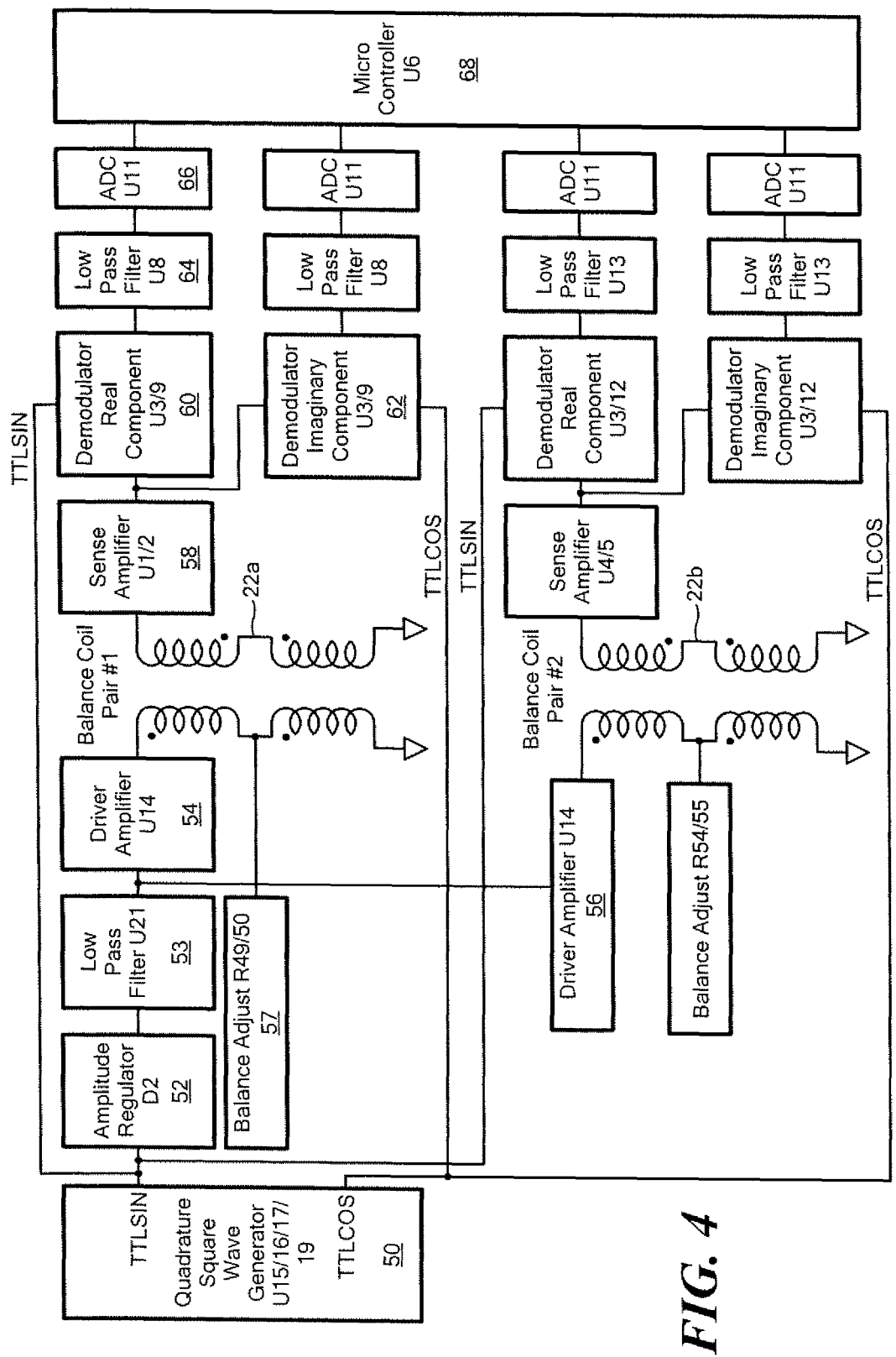
FIG. 4 is a schematic diagram of an example of the drive circuitry and impedance monitoring circuitry for the system of FIG. 1.

FIG. 4 illustrates the electronics of the subject invention. The Quadrature Square Wave Generator 50 generates a two-bit binary gray code. The sequence is 00, 01, 11, 10. Each state persists for about 11.4 microseconds, and the complete sequence repeats every 45 microseconds. The result is two pulse trains (TTLSON and TTLCOS), each having a frequency of 22 kHz and a duty cycle of 50%, and are thus square waves. There is an 11 microsecond delay between the two signals, equivalent to a phase shift of 90 degrees. The outputs have normal CMOS output levels.

The Amplitude Regulator 52 takes the square wave output from the Quadrature Square Wave Generator and produces a waveform having the same timing but having well-defined high and low voltage levels. This is done by creating two DC voltages, approximately 2.5 and 7.5V, in which the voltage difference between these two voltages is precisely controlled to be 5V. An analog switch alternates between these two voltages, producing a square wave with precisely controlled amplitude of 5V p-p.

The Low Pass Filter 54 is a three-pole Sallen-Key filter with a gain of 1.5 and a −3 db point of about 15 kHz. This filter attenuates the harmonics of the input square wave, making the waveform close to a sine wave.

The Driver Amplifiers 54 use high-power operational amplifiers in an inverting configuration. Their gain is 1.47, but this can be tailored for different applications. In their standard configuration, the output voltage is about 10V p-p.

The Balance Adjust network 57 consists of two potentiometers that are used to adjust the output of the coils so that the output is near zero when no sample is introduced into the cell. Each potentiometer is connected between the coil drive signal and ground. Thus the wiper of each potentiometer produces a voltage that is an adjustable fraction of the drive voltage. One potentiometer has a resistor connected from the wiper to the junction of the two drive coils. The second potentiometer has a capacitor connected from the wiper to the junction of the two drive coils. When the potentiometers are set with the wipers at half-scale, no current will flow through the resistor or the capacitor because both ends of the resistor or capacitor are at half of the drive voltage, and so the voltage across the resistor or capacitor is zero. If one of the potentiometers is adjusted away from this position, current will flow through the resistor or capacitor. Since the ac current through a capacitor is 90 degrees ahead of the current through a resistor, any phase or magnitude of adjustment is possible.

The Balance Coil is described elsewhere. In short it consists of two transformers with the primaries connected in series and the secondaries connected in anti-series. It is excited by the 10V p-p drive voltage and its output is nominally zero under balanced conditions (no sample in cell).

The sense amplifier 58 is a three-stage high gain amplifier having a gain of about 2000 and a band-pass characteristic. The first stage is a low-noise amplifier suited to amplifying the low-impedance output of the sense coils. Its gain is 100 and it has a low-pass characteristic. The second stage is a gain of ten bandpass, and the third stage is a gain of two bandpass.

Each channel has two demodulators 60, 62, one for the imaginary component and one for the real component. The two demodulators are used together to determine the size of a particle and to determine whether the particle is ferrous or conductive. Each demodulator consists of an inverting amplifier with a gain of −1, followed by an analog multiplexer. Each multiplexer alternately connects its output to either the input or the output of the inverting amplifier. The multiplexer's control input is driven by the output of the Quadrature Square Wave Generator. The output of the demodulator is thus sensitive to inputs at the frequency of the drive voltage, and rejects other frequency components in the signal. It is also phase sensitive, rejecting signals that are phase shifted by 90 degrees from the control signal.

The Low Pass Filter 64 is a MFB (Multiple Feedback) low-pass filter having a gain of 2 and a −3 db point of about 100 Hz. It smooths the output of the demodulator to produce a ripple-free waveform.

The ADC 66 converts the output of the filter to digital 'bin'. It is a 16-bit SAR (Serial Approximation Register) converter. The Micro Controller 68 takes the digital values from the four ADC's, formats them, and transmits them through a serial port.

It can be seen that the electronics provide for a two-channel instrument (magnetometer subsystems 22a and 22b each representing one channel) that uses the magnetic properties of a material in a carrier such as oil, to determine the material's size, concentration and composition. It operates by sensing the change in inductance of a coil when a small amount of ferrous or conducting material is introduced into a sample cell inside the coil.

It is desirable to detect the smallest possible quantity of material, and so it is necessary to detect a small change in inductance. The current embodiment can detect a change of about 1 part in $10^7$ in inductance.

For each channel, a dummy coil, having nominally the same characteristics as the sensing coil but not magnetically coupled to it, is put in series with the sensing coil, and an AC excitation voltage is applied to the series pair. Thus without any ferrous or conducting material, the voltage at the junction of the two coils would be half of the excitation voltage. Changes in the characteristics of the coils due to environmental conditions (such as temperature) would normally mask the small measurement, but with matched coils the output would remain at half of the excitation.

Though the dummy coil stabilizes the signal to be measured, it is still necessary to measure a very small voltage change (microvolts) on a large voltage (volts). This would require a measurement system stable to sub-ppm levels, which is not practical. To alleviate this requirement, each coil is provided with a secondary winding which is wound on top of the primary winding, with close magnetic coupling. Thus the secondary winding will generate a voltage which is closely proportional to the back EMF of the primary winding. Because these secondary coils are not electrically connected to the primary coils, the secondary of the sensing coil may be wired in anti-series with the secondary of the dummy coil. The net output of this pair is the difference between the back EMF's of the two coils.

Because of the matching of the two coils, this output voltage would be zero if no ferrous or conducting material is present. In practice the two coils would not be perfectly matched, and so the output would deviate from zero in proportion to the matching. There are also parasitic capacitances in the coils that unbalance the coil pair. In practice the output should be matched to within a small fraction of 1%. Even this small imbalance is many times larger than the signals to be measured. This imbalance is corrected in the electronics.

A ferrous particle changes the inductance of the coil, while a conducting particle changes the resistance of the coil. Thus the change in output voltage of the coil is 90° out of phase for the two types of particles. With appropriate signal processing, the phase of the voltage change can be measured and the two types of particles can be distinguished. The block diagram in FIG. 4 shows the major functional sections of the electronics. The description refers to the circuitry associated with coil pair #1 (associated with magnetometer subsystem 22a) unless noted.

The coils are excited with a 22 kHz pseudo-sine wave. A Quadrature Square Wave Generator 50 creates two digital square waves, TTLSIN and TTLCOS. In Amplitude Regulator 52, TTLSIN is used to generate another square wave having extremely stable amplitude characteristics. This square wave is passed through the Low Pass Filter 54 which attenuates the harmonics of the square wave. Since the harmonics are not completely removed, the waveform is not exactly sinusoidal, thus the label pseudo-sine. This signal is fed to Driver Amplifier 54 which changes the voltage and provides high current drive capability to drive the coil pair. Coil pair #2 (associated with magnetometer subsystem 22b) has its own amplifier 56 which may have a different gain to provide a different drive voltage to coil pair #2.

The Drive Amplifier connects to the series pair of coils. As noted above, the coil pair may be imbalanced and generate a non-zero output with the sample cell empty. The Balance Adjust circuit cancels this imbalance by injecting a small adjustable AC current into the junction between the two coils. The imbalance may have any phase, so two independently adjustable currents are injected. One is injected through a resistor, while the other is injected through a capacitor. The currents are 90° out of phase with each other, so by varying their amplitudes any imbalance may be cancelled.

As described above, the coil primaries are in series and the secondaries are in anti-series. This in combination with the imbalance adjustment provides an output signal that is typically in the range of 0-1 millivolt peak-to-peak. The Sense Amplifier 58 has a gain in the low thousands, and in addition provides several stages of high- and low-pass filtering.

The output of the Sense Amplifier is demodulated at 60 using and inverting amplifier and an analog switch. The inverting amplifier has a gain of −1, producing a 180° phase-shifted version of the sense amplifier output. The analog switch is driven by the TTLSIN signal, which is a square wave at the same frequency as the amplifier output. When TTLSIN is high, the amplifier output is selected, while when TTLSIN is low, the inverted output is selected. Thus an AC signal from the amplifier, having no DC component, is converted to a pulsating DC level that is proportional to the AC amplitude.

A second demodulator 62 is used to detect signals that are not in phase with TTLSIN and would not produce an output from the first demodulator. It works the same way as the first demodulator but is driven by TTLCOS, which is 90° out of phase with TTLSIN. The output of the two demodulators provides a real and imaginary component of a complex number that describes the magnitude and phase of the Sense Amplifier output.

Low Pass Filter 64 is used to eliminate the pulsations in the outputs of the Demodulators. It is a two-pole filter with a 100 Hz knee and a DC gain of 2.

ADC 66 converts the output of the Low Pass Filter. It is a 16-bit, 8 channel SAR type ADC with an internal 2.5V reference and a signal range of 0-2.5V. The ADC converts all four Filter outputs at a rate of 500 samples/second for each channel (total sample rate of 2000 samples/second). Since it is a single ADC with a multiplexer, the acquisition is not simultaneous. The skew is made as small as is convenient based on programming considerations, simply by taking each of the four samples in succession.

The microcontroller receives the ADC samples and formats the four 16-bit values into a comma separated ASCII stream terminated with <cr><lf>. The stream is sent out of a USB port with no handshaking. This USB port transmits the data from magnetometer subsystems 22a and 22b to the processor subsystem 20, FIG. 1. Transmission begins upon power-up of the microcontroller.

Figure 5:
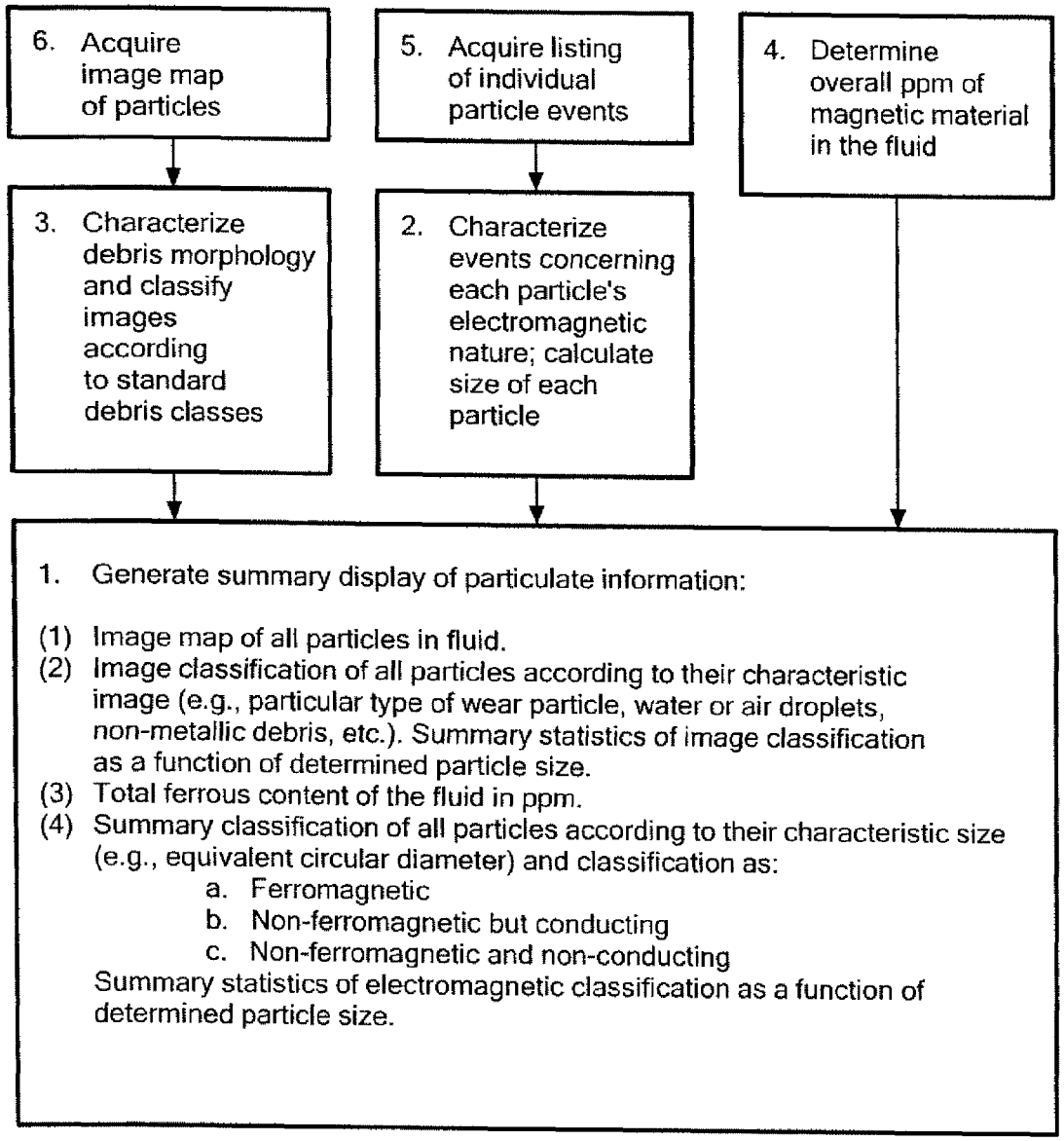
FIG. 5 is a flow chart depicting the primary steps associated with programming of the processor subsystem depicted in FIG. 1.

FIG. 5 shows the primary steps associated with the programming of processor subsystem 20, FIG. 1. The image processor utilizes, in one example, a k-nearest neighbor (k-NN) classification technique which is built from a library of known particle types, in classifying each particle as being wear (cutting, sliding, fatigue), non-metallic, fibrous, water or air. The image processor then classifies individual particles into size bins of equivalent circular diameter. It achieves this by calculating the measured area of the particle from the image itself and then calculating diameter of a circle with an equivalent area. The result is that each particle is tagged with both an equivalent diameter and type classification. Input from the first-stage magnetometer may serve as feedback to the k-NN to increase the number of nearest neighbors classified by 1, for example. The imaged particles can then be reclassified to determine if such an adjustment increased the number of particles classified as wear debris. This process can be repeated until the numbers provided by the imager and first-stage magnetometer at least coincide.

FIG. 5 describes the primary steps which are taken on the data acquired by each of the three subsystems which acquire information on the particle-laden fluid. For the imaging subsystem 20, an image map of each individual particle greater than 20 microns which are detected by the subsystem is generated. Such a map constitutes a sequential listing of all the particle images. With this in hand, the next step is to use the classification scheme of the system, which references a particle type library, in order to classify each particle in the map is being either wear-generated, non-metallic, fibrous, water or air. Depending on the needs of the system other such classification families may also be generated. The result of this analysis, and the determination of the size of the particle through calculating an equivalent circular diameter of the image, is then fed into the overall summary display.

For first stage magnetometer subsystem 22a, a listing of the particle events detected is generated. A particle event is typically characterized by a short-duration (~0.1 seconds) increase in the output voltage of the subsystem 22a. Such events are determined by a thresholding algorithm which examines events a number of standard deviations above the quiescent output of the subsystem 22a, and certifies them as actual events if their characteristic voltage vs. time signature is sufficiently different from a typical noise signature (determined dynamically on the output). These events are classified according to the electromagnetic nature of the event, i.e., it is determined if the event is from a primarily ferromagnetic particle or from a highly conducting particle. This is accomplished by examining the 2-channel output of the electronics and simply noting if the signal occurred on the imaginary channel (and hence is ferromagnetic) or the real channel (and so conducting). From this listing of events, the equivalent circular diameter of each particle is determined by a fixed, stored calibration of the net peak output voltage to equivalent circular diameter of the particle. The result is a listing of particle events, the size and electromagnetic nature of each event, which can then be fed into the overall summary display.

For the second stage magnetometer subsystem 22b, the overall part per million (ppm) weight of the fluid is determined. This is accomplished by recording the average output voltage (over a period of approximately 10 seconds) of the magnetometer 22b on the imaginary (ferromagnetic) output channel when fluid is injected into the flow line which travels through the coil. Next, the fluid is flushed out of the flow line and is replaced with cleaning fluid of a known type (such as Electron 22 solvent). The output voltage of 22b on the imaginary output channel is again recorded and averaged over a period of approximately 10 seconds. From the difference of these two voltages, a stored linear calibration to the overall ppm weight of the fluid to this resultant voltage provides the ppm outputted to the overall summary display.

The overall summary display is then utilized to provide information from all three measurement subsystems 20, 22a, and 22b, in a way that fuses this content to provide the most comprehensive information possible to the user. An example display is shown in FIG. 3. For each size bin, the following information is provided: (1) the total number of particles whose equivalent circular diameter is greater than or equal the size of that bin, (2) (if larger than 20 microns) the image classification summary statistics of (1), (3) the number (or percentage or both) of ferromagnetic and conducting particles in that same size bin. Also represented is the total ferrous content (in ppm) of the fluid. The images of the individual particles may also be present for viewing. A typical machinery wear situation illustrates the utility of fusing the information in this fashion: A significant amount of wear debris generated by the engine on large machinery, along with a small amount of dirt, may be present in the oil of a new engine upon startup. This would typically be reflected in elevated total particle counts in the small size bins, as well as elevated numbers of particles classified as wear debris and non-metallic. The wear debris particles identified at startup will be a mixture of ferromagnetic and conducting, so the total number of wear particles should be a split between ferromagnetic and conducting particles. The overall ferrous ppm reading may be slightly elevated at a reading of 20 ppm. As the engine heads towards a breakdown, an increasing total number of particles may be noted, along with an increasing number of particles in the larger size bins, as a percentage, relative to the numbers in the smaller diameter particle bins. The overall ferrous ppm reading will be continually elevated and may reach levels of 100 ppm. The larger particles are a sign that the engine itself is creating a large number of sliding and cutting wear debris particles. This contrasts with the profile that may be seen from an engine that has seen a significant amount of service but is not beginning a breakdown mode. Often, the engine oil will accumulate a significant amount of dirt due to its heavy usage and the aging of seals. In this case, all of the overall particle count levels may be similar, as well as the overall ferrous ppm reading (100 ppm). However, we will see a clear indication in the ferromagnetic particle count, which may be 20% of the total number of particles in given bin, even though there are significantly elevated overall counts in that same bin, including particles classified as wear debris.

Figure 6:
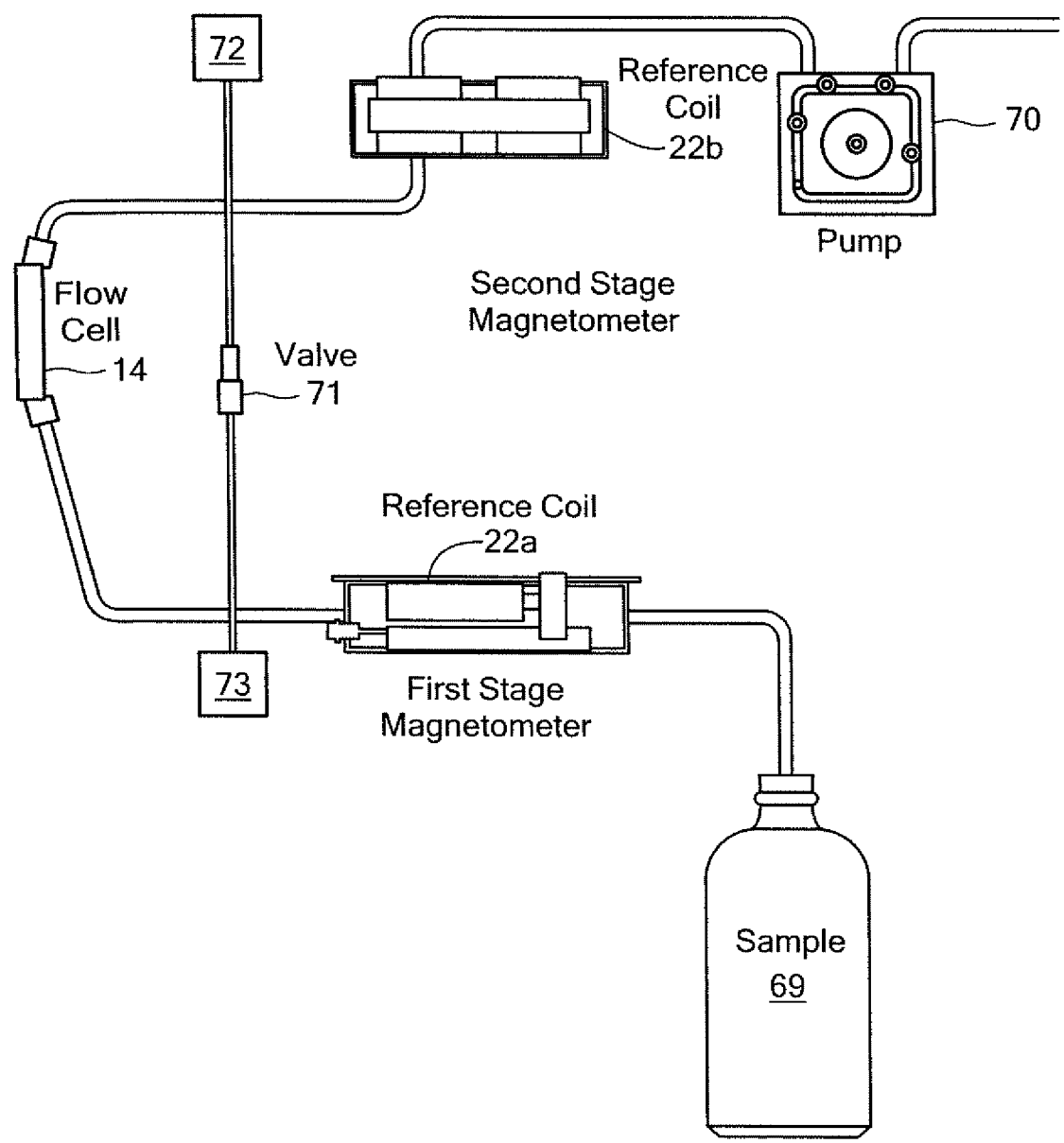
FIG. 6 is a mechanical drawing of one embodiment of the overall system.

FIG. 6 shows the fluid portion through the magnetometers and the flow cell imager. Fluid from a sample bottle 69 may be urged by a pump 70 through first-stage magnetometer 22a, flow cell 14, and second-stage magnetometer 22b. A valve 71 may be activated by pressure sensors 72, 73 when needed, typically to bypass the high flow restriction flow cell 14 for optimal cleaning.

Thus, although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A particle counter and classification system comprising:
    a detector subsystem configured to detect and determine the size of particles above a predetermined size in a fluid in a sample cell;
    a first stage magnetometer sensor subsystem for the fluid tuned to detect and determine the size of ferrous and/or conducting particles in said fluid above said predetermined size;
    a second stage magnetometer sensor subsystem for said fluid tuned to detect the overall ferrous particle content of the fluid; and
    a processor subsystem, responsive to the detector subsystem, the first stage magnetometer sensor subsystem, and the second stage magnetometer sensor subsystem, configured to calculate and report the number of particles in the fluid in a plurality of size ranges, the number of ferrous and/or conducting particles in said size ranges, and the overall ferrous content of the fluid, and further configured to classify individual particles detected by said detector subsystem and to reclassify said individual particles based on feedback information from said first stage magnetometer sensor subsystem.

2. The system of claim 1 in which the detector is a component of an imaging subsystem including a light source directing electromagnetic radiation into the sample cell and the detector is responsive to electromagnetic radiation emitted from the sample cell.

3. The system of claim 1 in which the first stage magnetometer sensor subsystem includes a small diameter fluid conduit upstream or downstream of the sample cell with a small diameter sense coil thereabout and the second stage magnetometer sensor subsystem includes a larger diameter fluid conduit downstream of the sample cell with a larger diameter sense coil thereabout.

4. The system of claim 3 in which the larger diameter fluid conduit is downstream of the small diameter fluid conduit.

5. The system of claim 3 in which the filling factor of the small diameter sense coil is optimized for ferrous and/or conducting particles imagable by the imaging subsystem.

6. The system of claim 3 in which the filling factor of the large diameter sense coil is optimized for ferrous particle sizes below and above said predetermined size.

7. The system claim 3 in which the first stage magnetometer sensor subsystem further includes an impedance monitor configured to detect the amplitude and phase of the voltage of the small diameter sense coil.

8. The system of claim 3 in which the second stage magnetometer sensor subsystem further includes an impedance monitor configured to detect the amplitude and phase of the voltage of the larger diameter sense coil.

9. The system of claim 3 in which the small diameter conduit is between 250 and 750 microns in diameter.

10. The system of claim 3 in which the larger diameter conduit is between 1,500 and 15,000 microns in diameter.

11. A particle counting and classification method comprising:
    detecting particles in a fluid to determine their size;
    detecting ferrous and/or conducting particles above a predetermined size and, for said ferrous and/or conducting particles above said predetermined size, counting the number of said ferrous and/or conducting particles in a plurality of size ranges;
    detecting ferrous particles above and below said predetermined size and calculating the overall ferrous particle content of said fluid;
    classifying individual particles; and
    reclassifying said individual particles based on identification of said individual particles as ferrous and/or conducting particles.

12. The method of claim 11 in which detecting includes directing electromagnetic radiation into the sample cell and detecting electromagnetic radiation emitted from the sample cell.

13. The method of claim 11 in which detecting ferrous and/or conducting particles above said predetermined size includes passing the fluid through a first stage magnetometer sensor subsystem with a small diameter fluid conduit having a small diameter sense coil thereabout and detecting ferrous and/or conducting particles above and below the predetermined size includes passing the fluid through a second stage magnetometer sensor subsystem with a larger diameter fluid conduit having a larger diameter sense coil thereabout.

14. The method of claim 13 in which the larger diameter fluid conduit is upstream or downstream of a small diameter fluid conduit.

15. The method of claim 13 in which the filling factor of the small diameter sense coil is optimized for ferrous and/or conducting imagable particles.

16. The method of claim 13 in which the filling factor of the large diameter sense coil is optimized for particle sizes above and below said predetermined size.

17. The method claim 13 in which detecting ferrous and/or conducting particles above said predetermined size includes detecting the amplitude and phase of the voltage of the small diameter sense coil.

18. The method of claim 13 in which detecting ferrous particles above and below the predetermined size includes detecting the amplitude and phase of the voltage of the larger diameter sense coil.

19. The method of claim 13 in which the small diameter conduit is between 250 and 750 microns in diameter.

20. The method of claim 13 in which the larger diameter conduit is between 1,500 and 15,000 microns in diameter.

21. A particle counting and classification method comprising:
    imaging a sample to determine the size and morphology of particles above a predetermined size in a fluid in a sample cell;
    detecting and determining the size of ferrous and/or conducting particles in said fluid above said predetermined size; and
    calculating and reporting the number of particles in the fluid in a plurality of size ranges, their morphology, their classification as a particular particle type according to their characteristic morphology and the number of ferrous and/or conducting particles in said size ranges, including:
initially classifying said particles in different size ranges based on imaging and adjusting said initial classification based on the detected and determined size of ferrous and/or conducting particles in said fluid above said predetermined size.

22. The system of claim 1 in which said individual particles are classified by morphology.

23. The system of claim 22 in which said morphology classification is cutting wear, sliding wear, fatigue wear, fibers, water droplets, or air bubbles.

24. The system of claim 1 in which said feedback information from said first stage magnetometer sensor subsystem includes identification of said individual particles as ferrous and/or conducting particles.

25. The system of claim 1 in which the overall ferrous content is validated by comparing information received from the first stage magnetometer sensor subsystem with information received from the second stage magnetometer sensor subsystem.

\* \* \* \* \*